United States Patent [19]
Gerhold et al.

[11] Patent Number: 4,996,387
[45] Date of Patent: Feb. 26, 1991

[54] DEHYDROGENATION PROCESS

[75] Inventors: Bruce W. Gerhold; Richard L. Anderson, both of Bartlesville, Okla.

[73] Assignee: Phillips Petroleum Company, Bartlesville, Okla.

[21] Appl. No.: 382,453

[22] Filed: Jul. 20, 1989

[51] Int. Cl.[5] .............................................. C07C 5/34
[52] U.S. Cl. .................................... 585/654; 585/444; 585/631; 585/660; 502/38; 502/50; 208/133; 208/134; 208/137; 208/138; 208/140
[58] Field of Search ...................... 208/132, 133, 134; 585/444, 631, 660, 654; 502/38, 50

[56] References Cited

U.S. PATENT DOCUMENTS

| | | | |
|---|---|---|---|
| 3,518,284 | 6/1970 | Foster | 260/346.4 |
| 3,725,493 | 4/1973 | Stine | 260/680 E |
| 4,069,272 | 1/1978 | Hutson, Jr. | 260/680 E |
| 4,191,846 | 3/1980 | Farha, Jr. et al. | 585/660 |
| 4,229,609 | 10/1980 | Hutson, Jr. et al. | 585/660 |
| 4,407,774 | 10/1983 | Schretzmann et al. | 376/300 |
| 4,513,162 | 4/1985 | Al-Muddarris | 585/654 |
| 4,581,339 | 4/1986 | Bhatt et al. | 502/38 |
| 4,613,715 | 9/1986 | Haskell | 585/412 |
| 4,704,497 | 11/1987 | Gottlieb et al. | 585/654 |
| 4,737,595 | 4/1988 | Jones et al. | 585/444 |
| 4,739,124 | 4/1988 | Ward | 585/659 |

Primary Examiner—Helane Myers
Attorney, Agent, or Firm—George F. Bogatie

[57] ABSTRACT

A process for producing a dehydrogenated hydrocarbon product stream by catalytically dehydrogenating a feed stream is disclosed. The process utilizes a plurality of dehydrogenation catalyst-filled tubes in a furnace with all of the tubes connected in parallel to a common product outlet conduit, so that the effluent of all of the tubes is contained in a common product stream. Essentially continuous regeneration of the dehydrogenation catalyst, is achieved by cyclically contacting a portion of the catalyst with an admixture of oxygen-containing regeneration gas and diluent while contacting the remaining portion of the catalyst with an admixture of hydrocarbon feed material and diluent, and wherein free hydrogen is added to react with the oxygen-containing regeneration effluent gas before the oxygen-containing effluent gas enters the product stream.

10 Claims, 2 Drawing Sheets

DEHYDROGENATION PROCESS

This invention relates to an improved process for the dehydrogenation of dehydrogenatable hydrocarbon feed. In one aspect it relates to a process for purification of a hydrocarbon product stream. In another aspect it relates to a process for removal of free oxygen that is introduced into the dehydrogenation product gas stream during catalyst regeneration.

BACKGROUND OF THE INVENTION

It is well known to dehydrogenate alkanes in the presence of a dehydrogenation catalyst comprising a Group VIII metal catalyst supported on a highly calcined catalyst support such as alumina, silica or a Group II metal aluminate spinel. In a particular process which causes minimal isomerization of product olefin or olefins, a mixed feed containing alkane and a diluent such as steam or nitrogen is contacted, in the absence of oxygen, with the dehydrogenation catalyst. In this process a plurality of parallel arranged catalyst-filled tubes, which are mounted in a furnace, are utilized to contact the feed and the catalyst under dehydrogenating conditions. Due to the endothermic nature of the dehydrogenation reaction the catalyst is rapidly cooled on contact with the feed. As the reaction proceeds carbon deposits on the catalyst necessitate regenerating the catalyst periodically.

In order to regenerate the catalyst without interruption of the furnace operation, alkane feed flow to a single tube or a group of the tubes is periodically turned off in conjunction with admitting a reactivation medium comprising a free oxygen-containing gas and steam which is supplied to the single tube or group of tubes being regenerated. Upon completion of a regeneration period for one tube or a group of tubes, where carbonaceous deposits on the catalyst are substantially burned off, alkane flow is restarted to the regenerated tubes and another tube or group of tubes is selected for regeneration. In this furnace design the effluent from all tubes is combined so that the oxygen-containing effluent from the tube or tubes being regenerated is mixed in a single gas transfer conduit with the product gas from the product gas-producing tubes.

Although the above described process has the advantage of continuous operation, it experiences the objectionable feature of oxygen-containing regeneration gas entering the hydrocarbon product stream. Under some dehydrogenation conditions the oxygen entering the hydrocarbon product stream can react with the hydrogen or hydrocarbons in the product stream. Under typical dehydrgenation conditions, however, the oxygen can accumulate in various downstream vessels causing potential explosive conditions in the downstream equipment.

Accordingly, it is an object of this invention to improve safety in operating a dehydrogenation process.

A further object of this invention is to increase the safety of a petroleum refining process and the method employed therein.

Another object of this invention is to provide a method for oxygen removal in a catalyst regeneration stage of a dehydrogenation process.

SUMMARY OF THE INVENTION

In accordance with this invention a continuous process for dehydrogenating a dehydrogenatable hydrocarbon is disclosed. The process comprises the steps of:

(a) feeding an admixture of said dehydrogenatable hydrocarbon and a diluent to at least two catalyst-containing tubes within a furnace chamber of a reactor;

(b) contacting said admixture with catalyst contained in said at least two catalyst-containing tubes in said furnace chamber under endothermic dehydrogenating conditions so as to establish at least two product-producing tubes;

(c) combining the effluent from each of said at least two product-producing tubes so as to form a common product stream;

(d) cyclically discontinuing the flow of said dehydrogenatable hydrocarbon and initiating flow of a free-oxygen containing gas under regeneration conditions while continuing the flow of diluent to at least one of said at least two product-producing tubes so as to establish at least one regenerating tube having a free-oxygen containing effluent and at least one product-producing tube;

(e) adding a free hydrogen-containing gas to the effluent of said at least one regenerating tube prior to combining the effluent of said at least one regenerating tube with the effluent of said at least one product-producing tube; and (f) wherein a sufficient quantity of hydrogen-containing gas is added to the effluent of said at least one regenerating tube in step (e) so as to react at least a portion of free oxygen contained in the effluent of said at least one regenerating tube with free hydrogen added in step (e) before the oxygen-containing effluent of said at least one regenerating tube is combined with the effluent of said at least one product-producing tube.

In a preferred embodiment of the invention a plurality of dehydrogenation catalyst-filled tubes, mounted in a furnace and connected in parallel to a common product outlet conduit, are utilized for contacting the catalyst with an admixture of an alkane and steam under dehydrogenating conditions. Essentially continuous regeneration of the dehydrogenation catalyst is achieved by cyclically discontinuing alkane feed flow to at least one of the catalyst-filled tubes while continuing the flow of steam. An oxygen-containing regeneration medium such as air is then admitted to regenerate the catalyst contained in the tube or tubes being regenerated. At least a portion of the free oxygen exiting the tube or tubes under regeneration is removed prior to entering the hydrocarbon product stream by adding free hydrogen to the oxygen-containing regeneration effluent gas under steam dilution conditions so that the hydrogen reacts with oxygen to form water in a very slow and controlled manner. After a regeneration period, alkane feed flow is resumed to the tubes with the regenerated catalyst, and another tube or a group of tubes is selected for regeneration.

Additional objects and advantages of the invention will be apparent from the following detailed description of the preferred embodiment of the invention as illustrated by the drawing in which:

DETAILED DESCRIPTION OF THE PREFERRED EMBODIMENT

Figure 1:
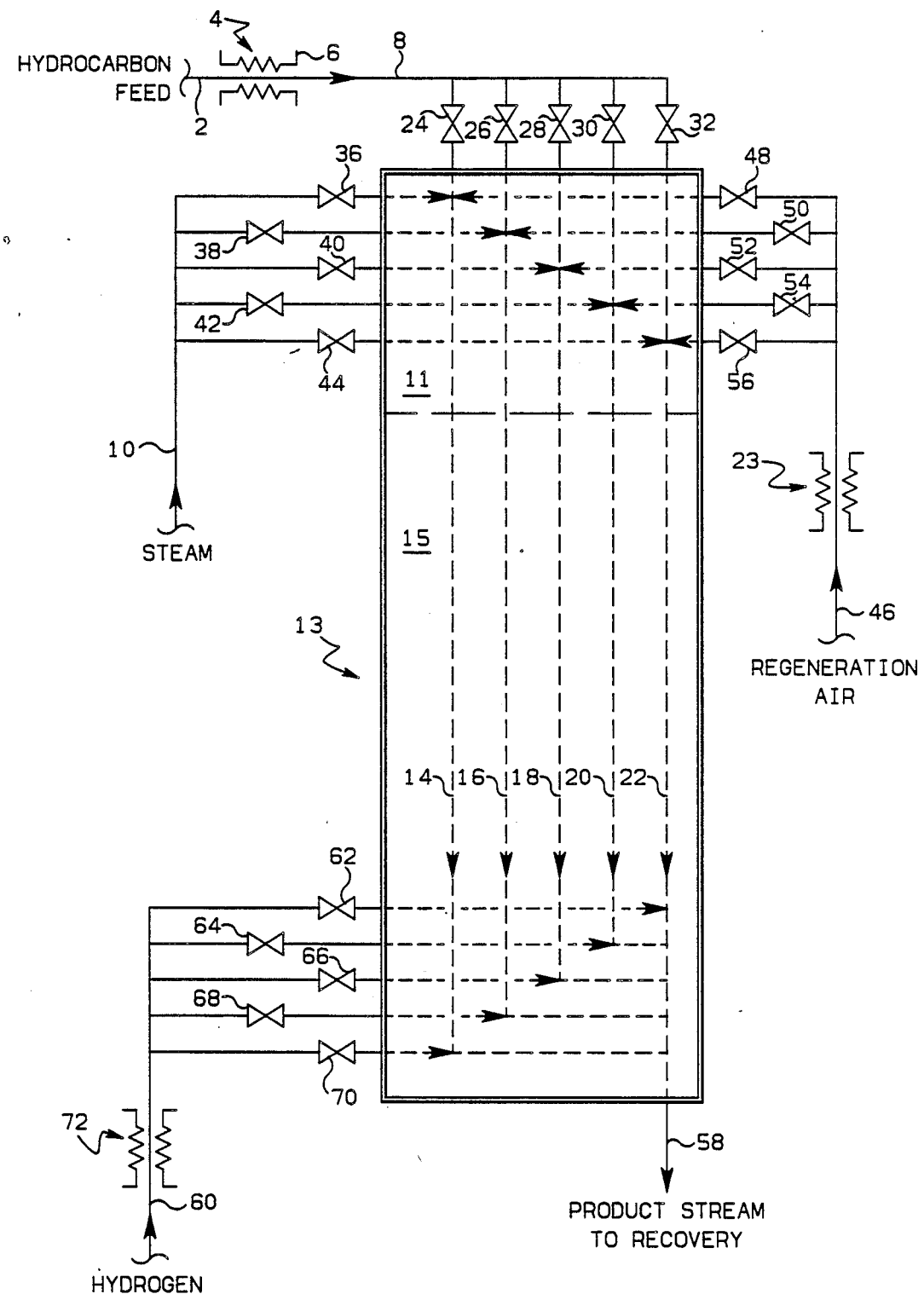
FIG. 1 is a schematic diagram illustrating process flow for a dehydrogenation process according to the invention.

It will be appreciated by those skilled in the art that, since FIG. 1 is schematic only, many items of equipment which would be needed in a commercial plant for successful operation, have been omitted for the sake of clarity. Such items of equipment would include, for example, temperature and pressure measurement instruments and corresponding process controllers, pumps, additional heat exchangers, and valves, etc., all these items would be provided in accordance with standard chemical engineering practice and form no part of the present invention.

The present invention is applicable to any dehydrogenation process employing more than one catalyst bed connected in parallel to a common product outlet conduit, and wherein the catalyst is regenerated by contact with an oxygen-containing gas.

Referring now to FIG. 1 a liquid alkane feed such as isobutane, but which can be any dehydrogenatable hydrocarbon, is supplied via conduit 2 to a vaporizer 4 which is supplied with a suitable heating medium such as steam via conduit 6.

The resulting gaseous isobutane in conduit 8 is admixed with steam from a separate preheating furnace, not illustrated, via conduit 10. FIG. 1 illustrates a simplified process in which the isobutane and steam are supplied via separate conduits to five dehydrogenation catalyst filled tubes 14, 16, 18, 20, and 22 within a furnace chamber 13. In practice, however, any desired number of tubes may be employed consistent with maintaining a desired pressure drop across the tubes.

The isobutane flowing in conduit 8 is divided and connects to catalyst-filled tubes 14-22 in a convective section 11 of furnace 13. Likewise steam flowing in conduit 10 is divided to supply tubes 14-22. Valves 24, 26, 28, 30, and 32 are arranged to shut off the flow of isobutane to one or more of the tubes as desired. Valves 36, 38, 40, 42, and 44 are arranged to shut off the flow of steam to the catalyst filled tubes 14-22 primarily for maintenance purposes, since in normal operation valves 36-44 would be in an open position to admit steam to the tubes 14-22 during both production and regeneration stages. Air which may be preheated in heater 23 is supplied via conduit 46 which, like conduits 8 and 10, is divided to supply tubes 14-22. Valves 48, 50, 52, 54, and 56 are arranged to shut off air flow to one or more of the tubes as desired. Thus for regenerating catalyst in one or more of the catalyst filled tubes 14-22, it is only necessary to to shut off the isobutane feed stream to those tubes while maintaining the steam supply and then adding the appropriate amount of air to the steam. Carbon is removed from the catalyst during regeneration in order to maintain catalyst activity. The number of tubes undergoing regeneration at any one time is determined as a function of the rate of catalyst deactivation. The remaining tubes not requiring regeneration are unaffected.

The dehydrogenation and regeneration steps are conducted under any suitable conditions. Examples of dehydrogenation and regeneration steps are disclosed, for example, in U.S. Pat. No. 4,229,609, the disclosure of which is incorporated herein by reference.

The effluent from all of the tubes, from both dehydrogenation and regeneration steps, is drawn off as a common product stream via conduit 58. For example, at any one time in operating the process, one tube can be regenerating while four tubes are dehydrogenating and all of the oxygen introduced into the system for regenerating the catalyst leaves in the mixed effluent flowing in conduit 58. This means that unless the oxygen reacts with hydrogen or hydrocarbon in conduit 58, an explosive mixture could form and possibly result in an explosion in the downstream product purification/recovery equipment.

In accordance with the invention, as illustrated in FIG. 1, a free hydrogen-containing gas is added via conduit 60 to the effluent of any tube or tubes undergoing regeneration. The free hydrogen, which can be supplied from any suitable source, is added in the radiant section 15 of furnace 13 at a point near the furnace exit of the catalyst-filled tube or tubes 14-22 undergoing regeneration, so as to react with the oxygen to form water prior to the regeneration effluent mixing with the hydrocarbon product effluent in conduit 58. The hydrogen flow in conduit 60 is divided so as to add hydrogen to the effluent of tubes 14-22, as desired, by opening one or more of valves 62, 64, 66, 68 or 70. Hydrogen flow through valves 62-70 is coordinated with the flow of free oxygen-containing gas through valves 48, 50, 52, 54, and 56. Hydrogen flow through conduit 60, which will generally be preheated in steam heater 72, may be initiated at the same time as initiation of the oxygen-containing gas to the tubes for regeneration, or alternately may be initiated during the steam purge period before regeneration actually begins. The effluent piping in the radiant section 15 of furnace 13, where the hydrogen is mixed with the tube effluent is arranged to allow a sufficient time period for the added hydrogen to react with the free oxygen in the regeneration effluent gases before the regeneration effluent gas mixes with the product gas.

Figure 2:
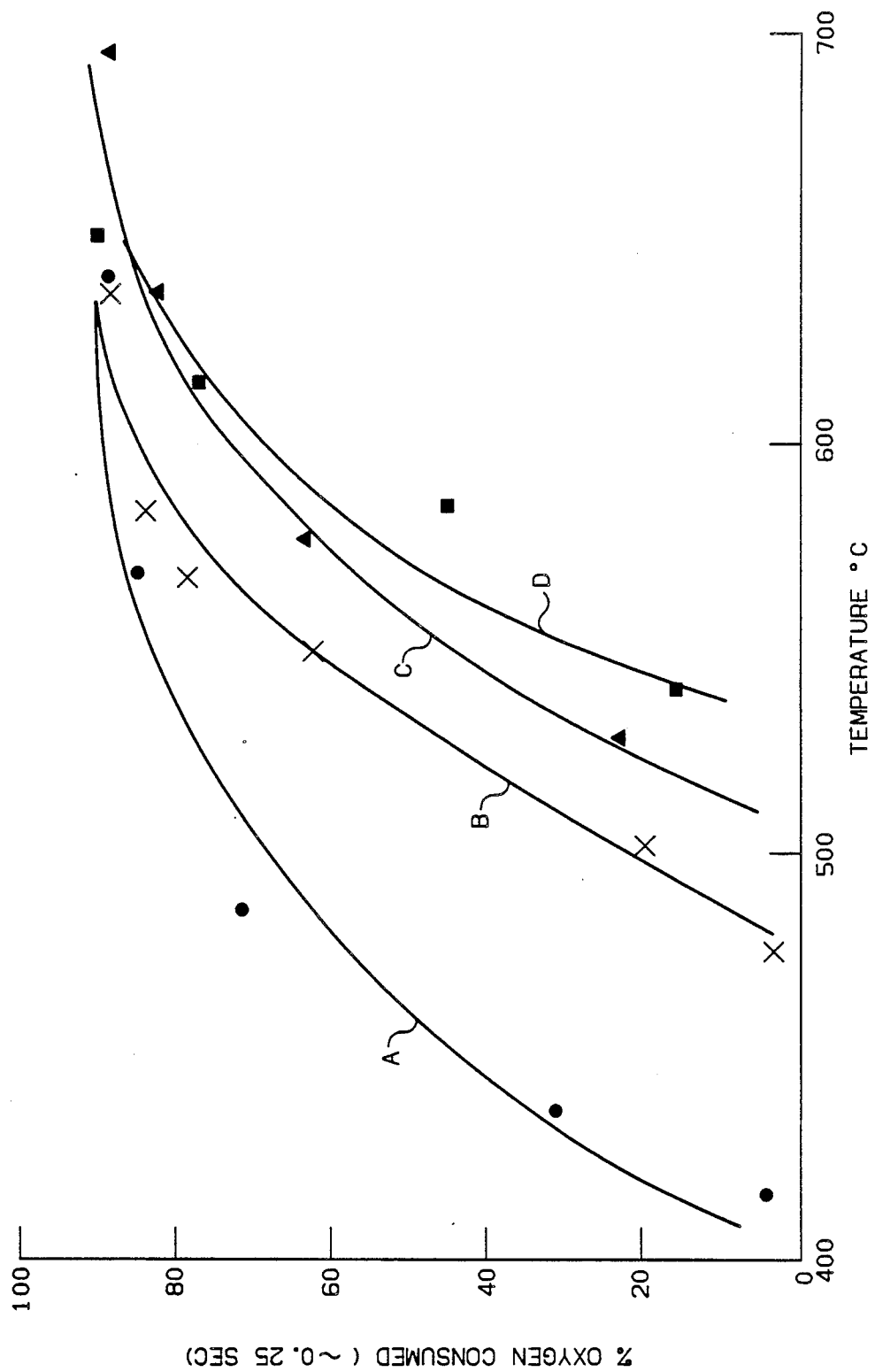
FIG. 2 is a plot of experimental data illustrating oxygen removal versus temperature under conditions which might exist in a commercial dehydrogenation process.

Referring now to FIG. 2 there is graphically displayed data illustrating oxygen removal from a process gas stream. The data were obtained under laboratory conditions that match as closely as possible the conditions that might exist in a commercial alkane dehydrogenation process. The experiment simulated conditions of adding a free hydrogen-containing gas, such as would be obtained by steam reforming natural gas in a small reformer tube, to the effluent of a dehydrogenation catalyst tube being regenerated by a steam-plus-air mixture. In a commercial operation the methane reformer tube could be located in the furnace adjacent to the dehydrogenation catalyst-filled process tubes. Table 1 below sets forth the composition in mole fractions of the gas tested which, for example, would correspond to the regeneration effluent gas entering the conduit junction 23 in FIG. 1 if catalyst-filled tube 22 was undergoing regeneration, and the free hydrogen-containing gas was admitted through valve 62.

TABLE

| Species | Low Air Flow | High Air Flow |
|---|---|---|
| $O_2$ | .019 | .005 |
| $H_2O$ | .712 | .766 |
| $H_2$ | .149 | .157 |
| $CO_2$ | .019 | .021 |
| CO | .011 | .011 |
| $CH_4$ | .019 | .020 |

TABLE-continued

| Species | Low Air Flow | High Air Flow |
|---|---|---|
| N₂ | .071 | .020 |

The two air flow rates correspond to different catalyst regeneration conditions. The experiments were run by allowing the test gas to reach a steady temperature with all gases flowing except air. The air was then turned on and an oxygen concentration measurement was recorded for the indicated flow rate, pressure and residence time. No pressure change was observed, which indicates that a well controlled homogenous reaction was taking place in a very dilute stream.

FIG. 2 illustrates removal of up to 90% of the oxygen present in a simulated regeneration effluent gas stream in a time period of about 0.25 seconds. Curve A illustrated in FIG. 2 was obtained at 1 atmosphere pressure with an oxygen concentration of 0.005 mol percent. Curve B in FIG. 2 was obtained at 1 atmosphere pressure with an oxygen concentration of 0.019 mol percent. Curve C was obtained at 20 PSIG with an oxygen concentration of 0.005 mol percent, and curve D at 20 PSIG with an oxygen concentration of 0.019 mol percent.

The invention has been described in terms of a dehydrogenation process which can be run essentially continuously using a single furnace containing a plurality of catalyst-filled tubes. An individual tube or tubes may be taken out of service at periodic intervals as required to reactivate the catalyst. Reasonable variations, modifications and adaptions for various usages and conditions can be made within the scope of the disclosure and the appended claims, without departing from the scope of this invention.

That which is claimed is:

1. A continuous process for dehydrogenating dehydrogenatable hydrocarbons comprising the steps of:
    (a) feeding an admixture of said dehydrogenatable hydrocarbon and a diluent to at least two catalyst-containing tubes within a furnace chamber of a reactor;
    (b) contacting said admixture with catalyst contained in said at least two catalyst-containing tubes in said furnace chamber under endothermic dehydrogenating conditions so as to establish at least two product-producing tubes;
    (c) combining the effluent from each of said at least two product-producing tubes so as to form a common product stream;
    (d) cyclically discontinuing the flow of said dehydrogenatable hydrocarbon and initiating flow of a free-oxygen containing gas under regeneration conditions while continuing the flow of diluent to at least one of said at least two product-producing tubes so as to establish at least one regenerating tube having a free-oxygen containing effluent and at least one product-producing tube;
    (e) adding a free hydrogen-containing gas to the effluent of said at least one regenerating tube prior to combining the effluent of said at least one regenerating tube with the effluent of said at least one product-producing tube; and
    (f) wherein a sufficient quantity of hydrogen-containing gas is added to the effluent of said at least one regenerating tube in step (e) so as to react at least a portion of free oxygen contained in the effluent of said at least one regenerating tube with free hydrogen added in step (e) before the oxygen-containing effluent of said at least one regenerating tube is combined with the effluent of said at least one product-producing tube.

2. A process in accordance with claim 1 wherein the residence time for said free hydrogen-containing gas added in step (e) to react with free oxygen in the effluent of said at least one regenerating tube prior to combining the effluent of said at least one regenerating tube with the effluent of said at least one product-producing tube is at least 0.2 sec.

3. A process in accordance with claim 2 additionally comprising the sequential steps of:
    discontinuing the flow of said free oxygen-containing gas to said at least one regenerating tube while continuing the flow of said diluent;
    restarting the flow of said dehydrogenatable hydrocarbon to said at least one regenerating tube, whereby said at least one regenerating tube becomes a product-producing tube; and
    repeating steps (d), (e), and (f) for another catalyst-containing tube.

4. A process in accordance with claim 2 wherein said step of adding a free hydrogen-containing gas to the effluent of said at least one regenerating tube comprises:
    feeding methane to a reformer tube in said furnace chamber; and
    combining the effluent of said reformer tube and the effluent of said at least one regenerating tube.

5. A process in accordance with claim 4 wherein the number of catalyst-containing tubes undergoing regeneration at any one time is dependent on the rate of catalyst deactivation.

6. A process in accordance with claim 5 wherein the dehydrogenatable hydrocarbon is selected from the group comprising propane, isobutane, n-butane, and n-pentane.

7. A process in accordance with claim 2 wherein said dehydrogenatable hydrocarbon consists essentially of hydrocarbons boiling in the gasoline range.

8. A process in accordance with claim 7 wherein the inlet portion of the catalyst contained in said catalyst-filled tubes is maintained at a temperature in the range of from about 510° C. to about 620° C. and the pressure is maintained in the range of from about 0 to about 200 psig for both dehydrogenation and regeneration steps.

9. A process in accordance with claim 8 wherein the catalyst in said catalyst-containing tubes comprises (1) a support selected from the group consisting of alumina, silica, magnesia, zirconia, alumina silicates, Group II aluminate spinels, and mixtures of any two or more, thereof and (2) a catalytic amount of at least one Group VIII metal selected from the group consisting of nickel, platinum, palladium, ruthenium iridium, rhodium, and osmium.

10. A process in accordance with claim 8 wherein said support is zinc aluminate spinel, and said Group VIII metal is platinum, and said catalyst further includes tin in an amount in the range of from about 0.01 to about 5 weight percent based on the weight of said zinc aluminate spinel and wherein said platinum is present in an amount of from about 0.1 to about 5 weight percent based on the weight of said zinc aluminate.

* * * * *